United States Patent [19]

Schönafinger et al.

[11] Patent Number: 5,166,166
[45] Date of Patent: Nov. 24, 1992

[54] 3-DICYCLOHEXYLAMINOSYDNONE IMINES, PROCESS FOR THEIR PREPARATION AND THEIR USE

[75] Inventors: Karl Schönafinger, Alzenau; Rudi Beyerle, Frankfurt; Helmut Bohn, Schöneck; Melitta Just, Langen, all of Fed. Rep. of Germany

[73] Assignee: Cassella Aktiengesellschaft, Frankfurt, Fed. Rep. of Germany

[21] Appl. No.: 730,456

[22] Filed: Jul. 16, 1991

[30] Foreign Application Priority Data

Aug. 13, 1990 [DE] Fed. Rep. of Germany ....... 4025604

[51] Int. Cl.$^5$ ................... A61K 31/41; C07D 271/04
[52] U.S. Cl. .................................... 514/364; 548/125
[58] Field of Search ........................ 548/125; 514/364

[56] References Cited

U.S. PATENT DOCUMENTS 5,006,540  4/1991  Schönafinger ................. 514/361
5,079,244  1/1992  Kujath ......................... 514/227.8

FOREIGN PATENT DOCUMENTS 1551013  12/1968  Fed. Rep. of Germany ...... 548/125
1942854   9/1970  Fed. Rep. of Germany ...... 548/125
7006016   2/1970  Japan ........................... 548/125

Primary Examiner—Robert Gerstl
Attorney, Agent, or Firm—Perman & Green

[57] ABSTRACT

The present invention relates to pharmacologically active substituted 3-dicyclohexylaminosydnone imines of the general formula I

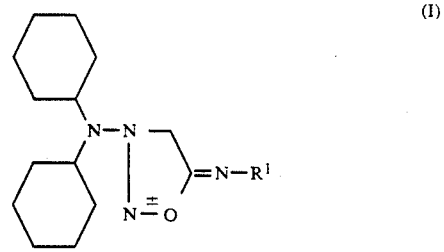

and their pharmacologically acceptable acid addition salts, in which $R^1$ denotes hydrogen or the radical —$COR^2$ and $R^2$ denotes ($C_1$ to $C_4$)-alkyl, ($C_1$ to $C_4$)alkoxy-($C_1$ to $C_4$)alkyl, ($C_1$ to $C_4$) alkoxy, ($C_1$ to $C_4$)alkoxy-($C_1$ to $C_4$)alkoxy, ($C_5$ to $C_7$)cycloalkyl, phenyl, a phenyl radical which is mono-, di- or trisubstituted by 1 to 3 halogen atoms and/or 1 to 3 alkyl radicals having 1 to 4 C atoms and/or 1 to 3 alkoxy radicals having 1 to 4 C atoms, a nicotinoyl radical or an allylmercaptoacetyl radical, and to a process for the preparation of the compounds according to the invention and their use.

5 Claims, No Drawings

3-DICYCLOHEXYLAMINOSYDNONE IMINES, PROCESS FOR THEIR PREPARATION AND THEIR USE

The invention relates to pharmacologically active substituted 3-dicyclohexylaminosydnone imines of the general formula I

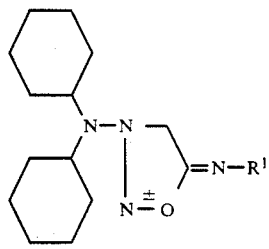

and their pharmacologically acceptable acid addition salts, in which $R^1$ denotes hydrogen or the radical —$COR^2$ and $R^2$ denotes ($C_1$ to $C_4$)-alkyl, ($C_1$ to $C_4$)alkoxy-($C_1$ to $C_4$)alkyl, ($C_1$ to $C_4$)alkoxy, ($C_1$ to $C_4$)alkoxy-($C_1$ to $C_4$)alkoxy, ($C_5$ to $C_7$)cycloalkyl, phenyl, a phenyl radical which is mono-, di- or trisubstituted by 1 to 3 halogen atoms and/or 1 to 3 alkyl radicals having 1 to 4 C atoms and/or 1 to 3 alkoxy radicals having 1 to 4 C atoms, a nicotinoyl radical or an allylmercaptoacetyl radical.

The invention furthermore relates to a process for the preparation of the compounds according to the invention and to their use.

Compounds structurally related to the compounds according to the invention have already been described in DE-A-1,670,127.

Alkyl radicals, alkoxyalkyl radicals, alkoxy radicals and alkoxyalkoxy radicals may be straight-chain or branched. This also applies if they occur as substituents of phenyl.

($C_1$ to $C_4$)Alkyl radicals may be: methyl, ethyl, n-propyl, i-propyl, n-butyl, i-butyl, tert.-butyl and sec.-butyl. Examples of ($C_1$ to $C_4$)alkoxy radicals may be: methoxy, ethoxy, n-propoxy, i-propoxy, n-butoxy, i-butoxy, sec.-butoxy and tert.-butoxy.

($C_1$ to $C_4$)Alkoxy-($C_1$ to $C_4$)alkyl radicals may be, for example: methoxymethyl, 2-methoxyethyl, 3-methoxypropyl, 4-methoxybutyl, 2-ethoxyethyl, 3-propoxypropyl, 4-propoxybutyl, 2-butoxyethyl, 3-butoxypropyl, 4-butoxybutyl, 3-i-propoxypropyl and 4-i-propoxybutyl.

($C_1$ to $C_4$)Alkoxy-($C_1$ to $C_4$)alkoxy radicals may be, for example: methoxymethoxy, 2-methoxyethoxy, 3-methoxypropoxy, 4-methoxybutoxy, 2-ethoxyethoxy, 3-propoxypropoxy, 4-propoxybutoxy, 2-butoxyethoxy, 3-butoxypropoxy, 4-butoxybutoxy, 3-i-propoxypropoxy, 4-i-propoxybutoxy and 2-i-propoxyethoxy.

Of the ($C_1$–$C_5$)-Cycloalkyl radicals, cyclopentyl and cyclohexyl are preferred.

Possible halogen atoms for the substituted phenyl radical are fluorine, chlorine, bromine and/or iodine, of which bromine and chlorine are preferred.

The substituted phenyl radical $R^2$ is preferably monosubstituted, in particular in the 2- or 4-position and/or by methoxy or chlorine. Preferred radicals for $R^2$ are ethoxy, p-methoxyphenyl, p-chlorophenyl, tert-butyl, 2-isopropoxyethoxy and allylmercaptoacetyl.

A compound of the general formula I can be prepared by cyclising the compound of the formula II

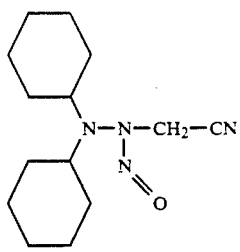

to give the compound of the general formula Ia

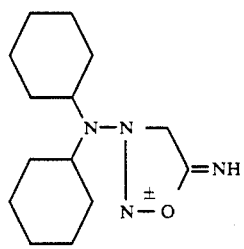

and in the case in which it is intended to prepare a compound of the formula I where $R^1$ = —$COR^2$, acylating this compound or an acid addition salt thereof with an acylating agent which introduces the radical —$COR^2$, and optionally converting the compound thus obtained into a pharmacologically acceptable acid addition salt.

The cyclisation of the compound II to give the compound Ia is carried out in a suitable organic or inorganic solvent, dispersant or diluent with the addition of a cyclising agent, normally at temperatures from —10° to 40° C., in particular 0 to 40° C., preferably at 0° to 20° C.

Suitable cyclising agents are those which establish a pH below 3 in aqueous solution, that is to say, for example, mineral acids, such as sulphuric, nitric or phosphoric acid, preferably hydrogen chloride, but also strong organic acids, such as trifluoroacetic acid. The cyclisation is normally carried out with ice-cooling.

0.1 to 10 mol, preferably 1 to 5 mol, of the cyclising agent is used, for example, relative to 1 mol of the compound of the formula II. The cyclising agent is normally employed in excess. The use of hydrogen chloride as a cyclising agent is particularly advantageous, and it is normally passed into the reaction mixture until it is saturated. The corresponding acid addition salt of the compound Ia is normally obtained in the cyclisation.

Suitable solvents, dispersants or diluents are, for example: alcohols, for example those having 1 to 8 C atoms, in particular those having 1 to 6 C atoms, preferably those having 1 to 4 C atoms, such as, for example, methanol, ethanol, i- and n-propanol, i-, sec- and tert-butanol, n-, i-, sec- and tert-pentanol, n-hexanol, 2-ethylbutanol, 2-ethylhexanol, isooctyl alcohol, cyclopentanol, cyclohexanol, methylcyclohexanol (mixture) and benzyl alcohol; ethers, in particular those having 2 to 8 C atoms in the molecule, such as, for example, diethyl ether, methyl ethyl ether, di-n-propyl ether, di-isopropyl ether, methyl n-butyl ether, methyl tert-butyl ether, ethyl propyl ether, di-butyl ether, tetrahydrofuran, 1,4- dioxane, 1,2-dimethoxyethane and bis-β-methoxyethyl ether; oligoethylene glycol dimethyl ethers, such as, for example, tetraglyme or pentaglyme; alkyl carboxylates, in particular those having 2 to 10 C atoms in the molecule, such as, for example, methyl, ethyl, butyl or isobutyl formate, methyl, ethyl, propyl, isopropyl, butyl, isobutyl or sec-butyl, amyl, isoamyl, hexyl, cyclohexyl or benzyl acetate or methyl, ethyl or butyl propionate; ketones, in particular those having 3 to 10 C atoms in the molecule, such as, for example, acetone, methyl ethyl ketone, methyl n-propyl ketone, diethyl ketone, 2-hexanone, 3-hexanone, di-n-propyl ketone, diiso-propyl ketone, di-iso-butyl ketone, cyclopentanone, cyclohexanone, methylcyclohexanone, dimethylcyclohexanone, benzophenone and acetophenone; aliphatic hydrocarbons, such as, for example, hexane and heptane, low- and high-boiling petroleum ethers, petroleum spirits and white spirit; cycloaliphatic hydrocarbons, such as, for example, cyclopentane, cyclohexane, methylcyclohexane, tetralin and decalin; aromatic hydrocarbons, such as, for example, benzene, toluene, o-, m- and p-xylene, and ethylbenzene; halogenated aliphatic or aromatic hydrocarbons, such as, for example, methylene chloride, chloroform, carbon tetrachloride, 1,2-dichloroethane, chlorobenzene and dichlorobenzene; hexamethylphosphoramide; sulphoxides, such as, for example, dimethyl sulphoxide; tetramethylene sulphone; and water. Mixtures of different solvents or dispersants may also be used, for example water-methanol or, preferably, ethyl acetatemethanol.

The compound of the formula Ia is the compound of the general formula I according to the invention in the case in which $R^1$ = hydrogen.

The acylation of the compound of the formula Ia, which may also be present in the form of an acid addition salt, in order to introduce the radical $R^1$ = —$COR^2$ can be carried out in a manner known per se using a suitable acylating agent of the formula III

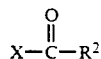

$$X-\overset{O}{\underset{\|}{C}}-R^2 \quad (III)$$

in which X represents a radical which can be eliminated nucleophilically.

In the formula III, X, for example, in particular denotes halogen, preferably —Cl or —Br; —OH; —O—alkyl, in particular having 1 to 5 C atoms; —O—aryl, the aryl radical in particular being a phenyl radical which may also be mono- or polysubstituted by alkyl, in particular methyl, and/or nitro, and is, for example, a tolyl, dinitrophenyl or nitrophenyl radical; —O—CO—$R^2$; —O—CO—O-alkyl, in particular having 1 to 5 C atoms in the alkyl radical, or the radical of an azole or benzazole which has at least 2 N atoms in the quasi-aromatic 5-membered ring and is bonded via an N atom.

The acylation is expediently carried out in a liquid or liquid disperse phase in the presence of an inert solvent, dispersant or diluent or in an excess of the acylating agent, expediently with stirring.

In the acylation, the molar ratio between the compound of the formula Ia and the acylating agent of the formula III is theoretically 1:1. However, the acylating agent can also be employed in excess or in a sub-equivalent amount. The acylating agent of the formula III is expediently employed in excess. Excesses of up to 30 mol % are usually sufficient, i.e. the molar ratio between the compound of the formula Ia and the acylating agent of the formula III is normally 1:(1 to 1.3), preferably 1:(1 to 1.2). If an acid is eliminated in the acylation reaction, the addition of an acid scavenger, such as, for example, an alkali metal hydroxide, such as, for example, sodium hydroxide, potassium hydroxide or lithium hydroxide, a tertiary organic amine, such as, for example, pyridine or triethylamine, an alkali metal carbonate or alkali metal bicarbonate, such as, for example, sodium carbonate or sodium bicarbonate, or an alkali metal salt of a weak organic acid, such as, for example, sodium acetate, is expedient. Suitable catalysts, such as, for example, 4-dimethylaminopyridine, may also be added during the acylation reaction.

The acylation may in principle be carried out at temperatures between −10° C. and the boiling point of the solvent, dispersant or diluent used. In many cases, the reaction is carried out at 0° to 50° C., in particular at 0° to 30° C. and preferably at room temperature.

The compounds of the formula III are acylating agents and thus represent, for example: for X=halogen: acid halides or haloformic acid esters, of which acid chlorides and chloroformic acid esters are preferred; for —OH: carboxylic acids; for —O—alkyl and —O—aryl: esters, of which the tolyl, 2,4-dinitro- or 4-nitrophenyl esters are preferred; for —O—CO—$R^2$: anhydrides; for —O—CO—O-alkyl: mixed carboxylic acid/carbonic acid anhydrides; or heterocyclic amides or azolides, in particular of N,N'-carbonyldiazoles, such as, for example, N,N'-carbonyldiimidazole, 2,2'-carbonyl-1,2,3-ditriazole, 1,1'-carbonyl-1,2,4-ditriazole, N,N'-carbonyldipyrazole and 2,2'-carbonylditriazole (compare, for example, H. A. Staab, M. Lücking and F. H. Dürr, Chem. Ber. 95, (1962), 1275 et seq., H. A. Staab and A. Mannschreck, Chem. Ber. 95, (1962), 1284 et seq.; H. A. Staab and W. Rohr, "Synthesen mit heterocyclischen Amiden (Azoliden)" [Syntheses with heterocyclic amides (azolides)] in "Neuere Methoden der Präparativen Organischen Chemie" [Newer methods of preparative organic chemistry], volume V, Verlag Chemie, 1967, p. 53 et seq., in particular pp. 65 to 69). The acylating agents of the formula III can be prepared by processes which are known per se.

When using a carboxylic acid as the acylating agent, the addition of an activating agent which has the object of increasing or of activating the acylating potential of the carboxylic acid or of converting the carboxylic acid into a reactive carboxylic acid derivative of the formula III in situ or preferably shortly before the reaction with the compound of the formula Ia is expedient. Suitable activating agents of this type are, for example: N,N'-disubstituted carbodiimides, in particular if they contain at least one secondary or tertiary alkyl radical, such as, for example, diisopropyl-, dicyclohexyl- or N-methyl-N'-tert.-butylcarbodiimide (compare Methodicum Chimicum, Verlag G. Thieme, Stuttgart, Vol. 6, (1974), pp. 682/683, and Houben-Weyl, Methoden der Org. Chemie [Methods of organic chemistry], Vol. 8, (1952), pp. 521/522); carbonic acid derivatives, such as, for example, phosgene, chloroformic acid esters, in particular having 1 to 5 C atoms in the alkyl radical (compare, for example, Tetrahedron Letters 24 (1983), 3365 to 3368); carbonic acid esters, such as, for example, N,N'-disuccinimidyl carbonate, diphthalimidyl carbonate, 1,1'-(carbonyldioxy)dibenzotriazole or di-2-pyridyl carbonate (compare, for example, Tetrahedron Letters, Vol. 25, No. 43, 4943-4946), if desired in the presence of suitable catalysts, such as, for example, 4-dimethylaminopyridine. In addition, N,N'-carbonyldiazoles, such as, for example, N,N'-carbonyldiimidazole, 2,2'-carbonyl-1,2,3-ditriazole, 1,1'-carbonyl-1,2,4-ditriazole, N,N'-carbonyldipyrazole, 2,2'-carbonylditetrazole, N,N'-carbonylbenzimidazole or N,N'-carbonylbenzotriazole are suitable as activating agents (compare, for example, H. A. Staab, M. Lücking and F. H. Dürr, loc. cit; H. A. Staab and A. Mannschreck loc. cit.; H. A. Staab and W. Rohr loc. cit). The N,N'-carbonyldiazole used is frequently the commercially available N,N'-carbonyldiimidazole. However, the other N,N'-carbonylazoles are also easily accessible from the respective azole and phosgene.

In addition, suitable activating agents for carboxylic acids are: derivatives of oxalic acid, such as, for example, oxalyl chloride (compare, for example, GB Patent Specification 2,139,225) or N,N'-oxalyldiazoles, such as, for example, 1,1'-oxalyldiimidazole, 1,1'-oxalyldi-1,2,4-triazole and 1,1'-oxalyldi-1,2,3,4-tetrazole (compare, for example, Shizuaka Murata, Bull. Chem. Soc. Jap. 57, 3597-3598 (1984)); methylethylphosphinic anhydride (compare, for example, German Offenlegungsschrift 3,101,427); diphosphorus tetraiodide (Chem. Lett. 1983, 449); dialkyl disulphite (Indian J. Chem. 21, 259 (1982)); or other reactive agents.

Suitable solvents, dispersants or diluents are, for example, those which have been mentioned for carrying out the cyclisation, and moreover also, for example, pyridine and amides, such as, for example, dimethylformamide. In addition to water, polar organic solvents, such as dimethylformamide, dimethyl sulphoxide or pyridine, are preferred for the acylation. Solvent mixtures, such as, for example, a mixture of water and methylene chloride, are also suitable.

The compounds of the general formula I can form acid addition salts with inorganic or organic acids. For the formation of pharmacologically acceptable acid addition salts, suitable acids are, for example: hydrogen chloride, hydrogen bromide, naphthalene-disulphonic acids, in particular 1,5-naphthalenedisulphonic acid, phosphoric, nitric, sulphuric, oxalic, lactic, tartaric, acetic, salicylic, benzoic, formic, propionic, pivalic, diethylacetic, malonic, succinic, pimelic, fumaric, maleic, malic, sulphamic, phenylpropionic, gluconic, ascorbic, isonicotinic, methanesulphonic, p-toluenesulphonic, citric or adipic acid. The acid addition salts may be prepared in a customary manner by combining the components, expediently in a suitable solvent or diluent.

The acid addition salts are normally obtained in the compound of the formula Ia. The free compound of the general formula Ia can be obtained from the acid addition salts, if desired, in a known manner, i.e. by dissolving or suspending it in water and rendering alkaline, for example with sodium hydroxide solution, and then isolating.

The starting compound of the general formula II may be prepared in a manner known per se by the following reaction scheme:

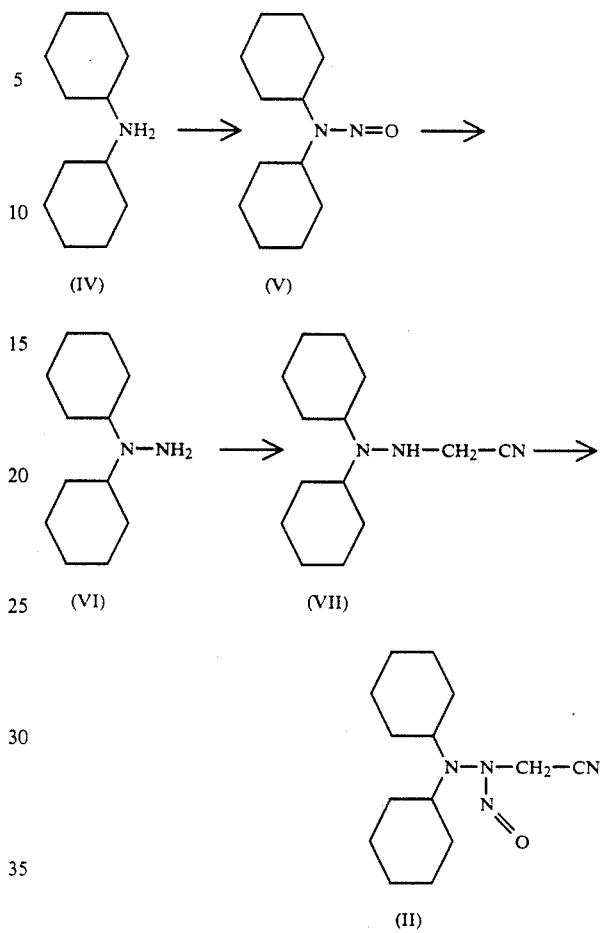

Accordingly, dicyclohexylamine of the formula IV is nitrosylated with nitrous acid and the N-nitrosodicyclohexylamine of the formula V obtained is reduced to N,N-dicyclohexylhydrazine of the formula VI. The latter is cyanomethylated to give the compound of the formula VII and this is finally nitrosylated to give the compound of the formula II.

The nitrosylations are carried out in a known manner, preferably in water, for example at temperatures from 0° to 10° C. The nitrous acid is in this case normally generated from an alkali metal nitrite, for example sodium nitrite, and hydrochloric acid. It is expedient to adjust the aqueous solution of the precursors to a pH of 1 to 3 with hydrochloric acid and to add the alkali metal nitrite dropwise in the form of an aqueous solution to the stirred and cooled solution of the compound.

The reduction of the compound of the formula V to the compound of the formula VI is carried out in a manner known per se with lithium aluminium hydride, with Zn dust in glacial acetic acid or with sodium in alcohol. However, other processes known from the literature can also be used.

Cyanomethylation to give the compound of the formula VII is carried out in a likewise known manner by reaction of the compound of formula VI with formaldehyde and hydrocyanic acid or sodium cyanide in a suitable solvent, for example water.

The compound of the formula IV is commercially available.

The compounds of the general formula I and their pharmacologically acceptable acid addition salts have useful pharmacological properties, for example haemodynamic, platelet function-inhibiting and antithrombotic, in particular coronary antithrombotic, properties. Their action on the cardiovascular system is particularly pronounced. Compared with known sydnone imine compounds substituted in the 3-position in a structurally similar manner, they unexpectedly have a surprisingly longer duration of action. For example, they lower the blood pressure as well as the pulmonary artery pressure and the left ventricular end-diastolic pressure and thus contribute to a relief of the load on the heart in the sense of an antianginal action, without provoking reflex tachycardia at the same time.

The compounds of the formula I and their pharmacologically acceptable acid addition salts can therefore be administered to humans as medicaments by themselves, in mixtures with one another or in the form of pharmaceutical preparations which permit enteral or parenteral use and which contain as the active component an effective dose of at least one compound of the formula I or an acid addition salt thereof, in addition to customary pharmaceutically innocuous excipients and additives.

The medicaments can be administered orally, for example in the form of pills, tablets, film tablets, coated tablets, hard and soft gelatin capsules, solutions, syrups, emulsions or suspensions or aerosol mixtures. Administration may, however, also be carried out rectally, for example in the form of suppositories, or parenterally, for example in the form of injection solutions, or percutaneously, for example in the form of ointments or tinctures.

The pharmaceutical preparations can be prepared using pharmaceutically inert inorganic or organic excipients. For the preparation of pills, tablets, coated tablets and hard gelatin capsules, for example lactose, maize starch or derivatives thereof, talc, stearic acid or its salts can be used. Excipients for soft gelatin capsules and suppositories are, for example, fats, waxes, semi-solid and liquid polyols, natural or hardened oils etc. Suitable excipients for the preparation of solutions and syrups are, for example, water, sucrose, invert sugar, glucose, polyols, etc. Suitable excipients for the preparation of injection solutions are, for example, water, alcohols, glycerol, polyols or vegetable oils.

The pharmaceutical preparations may also contain, in addition to the active compounds and excipients, further additives, such as, for example, fillers, extenders, disintegrants, binders, glidants, wetting agents, stabilisers, emulsifiers, preservatives, sweeteners, colourings, flavourings or aromatisers, buffer substances, additionally solvents or solubilisers or agents for achieving a depot effect or agents, as well as salts for changing the osmotic pressure, coating agents or antioxidants. They may also contain two or more compounds of the formula I or their pharmacologically acceptable acid addition salts and also other therapeutically active substances.

Examples of other therapeutically active substances of this type are: β-receptor blockers, such as, for example, propranolol, pindolol, metoprolol; vasodilators, such as, for example, carbochromen; tranquilisers, such as, for example, barbituric acid derivatives, 1,4-benzodiazepines and meprobamate; diuretics, such as, for example, chlorothiazide; cardiotonic agents, such as, for example, digitalis preparations; hypotensive agents, such as, for example, hydralazine, dihydralazine, prazosine, clonidine, Rauwolfia alkaloids; agents which lower the fatty acid level in the blood, such as, for example, bezafibrate, fenofibrate; and agents for thrombosis prophylaxis, such as, for example, phenprocoumon.

The compounds of the formula I, their pharmacologically acceptable acid addition salts and pharmaceutical preparations which contain the compounds of the formula I or their pharmacologically acceptable acid addition salts as active compounds can be used in humans for controlling or preventing diseases of the cardiovascular system, for example as antihypertensive medicaments in the various forms of high blood pressure, and in the control or prevention of angina pectoris etc. The dosage may vary within wide limits and is to be suited to the individual requirements in each individual case. In general, a daily dose of about 0.5 to 100 mg, preferably 1 to 20 mg, per human individual is suitable for oral administration. For other administration forms, the daily dose, owing to the good absorption of the active compounds, is also in similar amount ranges, i.e. in general also 0.5 to 100 mg/ human. The daily dose is normally divided into several, for example 2 to 4, part administrations.

The pharmacological action of the compounds of the formula I was determined by a modified method of Godfraind and Kaba (Arch. Int. Pharmacodyn. Ther. 196, (Suppl) 35 to 49, 1972) and of Schüman et al. (Naunyn-Schmiedeberg's Arch. Pharmacol. 289, 409 to 418, 1975). In this connection, spiral strips of the pulmonary artery of the guinea-pig are depolarised with 40 mmol/l of potassium after equilibration in calcium-free Tyrode solution. An addition of 0.5 mmol/l of $CaCl_2$ then induces a contraction.

The relaxing action of the test substance is determined by cumulative addition in ½ log 10 stepped concentrations. From the concentration-effect curve (abscissa: −log mol/l of test substance, ordinate: % inhibition of the maximum contraction, average value of 4 to 6 vessel strips), the concentration of the test substance is determined which inhibits the contraction by 50% (=$IC_{50}$, mol/l). The duration of action of the test substance is given by the time which is needed after the addition of the test substance until the starting value is obtained again. The values thus obtained are indicated in the following table.

| | $IC_{50}$ | Duration of action in minutes |
|---|---|---|
| 3-Dicyclohexylaminosydnone imine hydrochloride | $4 \times 10^{-7}$ | 270 |
| N-p-Anisoyl-3-dicyclohexyl-aminosydnone imine | $3 \times 10^{-6}$ | 300 |
| N-Pivaloyl-3-dicyclohexyl-aminosydnone imine | $5 \times 10^{-6}$ | 310 |
| 1st comparison substance: Molsidomine | $3 \times 10^{-4}$ | 120 |
| 2nd comparison substance: SIN-1 | $1 \times 10^{-6}$ | 90 |

Molsidomine = N-Ethoxycarbonyl-3-morpholinosydnone imine
SIN-1 = 3-Morpholinosydnone imine hydrochloride

EXAMPLES 1. 3-Dicyclohexylaminosydnone imine hydrochloride a) 2. N-Nitrosodicyclohexylamine A solution of 20.7 g of sodium nitrite in 60 ml of water is slowly added dropwise at RT to a mixture of 36.2 g of dicylohexylamine, 18 ml of conc. HCl and 300 ml of water. After this, the mixture is heated to 95° C. for 7 h. The nitro compound is extracted by shaking with ether. After drying over Na$_2$SO$_4$ and evaporating the ether, an oily residue remains which immediately crystallises.

Yield: 23 g.

m.p. 102° to 103° C.

b) N,N-Dicyclohexylhydrazine hydrochloride

A total of 25 g of lithium aluminium hydride is gradually added at 90° C. under nitrogen as inert gas to a mixture of 126 g of N-nitrosodicyclohexylamine, 1.2 l of dibutyl ether and 300 ml of tetrahydrofuran and the mixture is then stirred at 90° C. until completion of the reaction. After cooling to 5° C., it is cautiously hydrolysed with 50 ml of water, the solid components are filtered off with suction and the filtrate is concentrated in vacuo. An oil remains, which is converted into the hydrochloride by dissolving in ether and introducing HCl gas.

Yield: 133 g.

m.p.: 124° C. (dec.).

c) N,N-Dicyclohexylamino aminoacetonitrile

A suspension of 2.5 g N,N-dicyclohexylhydrazine hydrochloride in 75 ml of H$_2$O is treated with 0.75 g of sodium cyanide and with 1.2 g of a 39% strength formalin solution. This mixture is stirred at pH=6 to 7 at RT for 4 h. The product is removed by shaking with ethyl acetate and, after drying the organic phase, precipitated as the hydrochloride.

Yield: 1.5 g.

m.p 173° C. (dec.).

d) 3-Dicyclohexylaminosydnone imine hydrochloride

The compound (1.5 g) prepared in Example 1c is dissolved in 50 ml of water under nitrogen. After adding 50 ml of ethyl acetate, the solution is treated with 0.6 g of NaNO$_2$ and a pH of 1 to 2 is established. After reaction is complete, the ethyl acetate phase is removed, dried over Na$_2$SO$_4$ and the product is precipitated by addition of excess isopropanolic hydrochloric acid.

Yield: 1.0 g.

m.p.: 154° C. (dec.).

2. N-Pivaloyl-3-dicyclohexylaminosydnone imine

A mixture of 3 g of 3-dicyclohexylaminosydnone imine hydrochloride (Example 1d), 50 ml of water and 2.1 g of sodium bicarbonate is combined at 0° to 5° C. with a solution of 1.5 g of pivaloyl chloride in 40 ml of methylene chloride and the mixture is stirred at increasing temperature for 6 h. The organic phase is removed, dried over MgSO$_4$ and concentrated. The residue which remains is recrystallised from petroleum ether.

Yield 1.96 g.

m.p.: 110° C.

The following compounds were prepared in an analogous manner:

3. N-Isopropoxyethoxycarbonyl-3-dicyclohexylaminosydnone imine

M.p.: 107° C. by reaction with isopropoxyethyl chloroformate.

4. N-p-Chlorobenzoyl-3-dicyclohexylaminosydnone imine

M.p.: 112° to 114° C. by reaction with p-chlorobenzoyl chloride.

5. N-Ethoxycarbonyl-3-dicyclohexylaminosydnone imine

M.p.: 92° C. by reaction with ethyl chloroformate.

6. N-p-Anisoyl-3-dicyclohexylaminosydnone imine

M.p.: 160° C. by reaction with p-anisoyl chloride.

7. N-Allylmercaptoacetyl-3-dicyclohexylaminosydnone imine

M.p.: Oil by reaction with allylmercaptoacetyl chloride.

8. N-Nicotinoyl-3-dicyclohexylaminosydnone imine

M.p.: 170° to 172° C. by reaction with nicotinoyl chloride.

It is to be understood that the above described embodiments of the invention are illustrative only, and that modifications thereof may occur to those skilled in the art. Accordingly, this invention is not to be regarded as limited to the embodiments disclosed herein, but is to be limited only as defined by the appended claims.

We claim:

1. Substituted 3-dicyclohexylaminosydnone imines of the general formula I

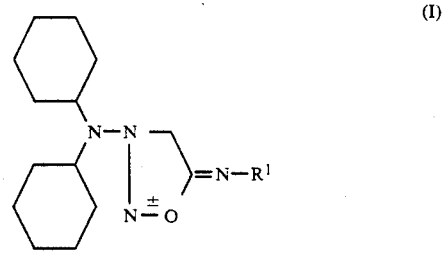

and their pharmacologically acceptable acid addition salts, in which R$^1$ denotes hydrogen or the radical —COR$^2$ and R$^2$ denotes (C$_1$ to C$_4$)-alkyl, (C$_1$ to C$_4$)alkoxy-(C$_1$ to C$_4$)alkyl, (C$_1$ to C$_4$)alkoxy, (C$_1$ to C$_4$)alkoxy-(C$_1$ to C$_4$)-alkoxy, (C$_5$ to C$_7$)cycloalkyl, phenyl, a phenyl radical which is mono-, di- or trisubstituted by 1 to 3 halogen atoms and/or 1 to 3 alkyl radicals having 1 to 4 C atoms and/or 1 to 3 alkoxy radicals having 1 to 4 C atoms, a nicotinoyl radical or an allylmercaptoacetyl radical.

2. Substituted 3-dicyclohexylaminosydnone imines according to claim 1, characterised in that R$^2$ denotes ethoxy, p-methoxy-phenyl, p-chlorophenyl, tert-butyl, 2-isopropoxyethoxy or allylmercaptoacetyl.

3. 3-Dicyclohexylamino-syndnone imine hydrochloride.

4. Pharmaceutical preparation for the treatment and control of hypertension and/or angina pectoris, characterised in that it contains an effective amount of a substituted 3-dicyclohexylaminosydnone imine of the general formula I according to claim 1 and/or 2 or a pharmacologically acceptable acid addition salt thereof as an active compound together with pharmaceutically acceptable excipients and additives and, optionally, one or more other pharmacological active compounds.

5. Process for the control and treatment of hypertension and/or angina pectoris which comprises administering to a host in need thereof an effective dose of a substituted 3-dicyclohexylaminosydnone imine of the general formula I according to claim 1, or a pharmacologically acceptable acid addition salt thereof.

* * * * *